United States Patent [19]

Kirsch

[11] Plant 4,606

[45] Oct. 28, 1980

[54] LILY PLANT NAMED GOLD DUST

[75] Inventor: Ted T. Kirsch, Myrtle Point, Oreg.

[73] Assignee: Sun Valley Bulb Farms, Inc., Myrtle Point, Oreg.

[21] Appl. No.: 62,316

[22] Filed: Jul. 30, 1979

[51] Int. Cl.[3] ..... A01H 5/00
[52] U.S. Cl. ..... Plt./68
[58] Field of Search ..... Plt./68

*Primary Examiner*—Robert E. Bagwill
*Attorney, Agent, or Firm*—Charles W. Rummler

[57] ABSTRACT

A new variety of Asiatic hybrid lily plant of the chalice type particularly distinguished by its one-quarter to one-half inch wide golden yellow stripe which runs longitudinally down the middle of each of the red-orange petals of its five to six inch diameter flowers, the flowers being borne in raceme arrangement on strong, upright pedicels, usually with one bud or flower on each pedicel, carried on strong stems which grow up to three feet tall, depending upon the age of the bulb.

1 Drawing Figure

BACKGROUND OF THE NEW PLANT

My new lily plant originated as a mutant seedling of the variety Enchantment (U.S. Plant Pat. No. 862) and was discovered by me at my nursery in Arcata, Calif., among a field of the variety Enchantment being grown for commercial purposes. The pollen parent of this new lily is unknown but the similarity to the variety Enchantment prompted me to asexually propagate the new plant for study of its growth habit and blooming characteristics, with the result that I have found the new plant to have distinctive and advantageous characteristics which distinguish it from Enchantment and appear to make it a valuable addition to the field of commercial lily plant culture. Further propagation of this new lily plant through successive generations by means of scales and tissue culture at Arcata, Calif., has shown that its distinctive characteristics hold true from generation to generation and appear to be firmly fixed.

DESCRIPTION OF THE DRAWING

This new variety of lily plant is illustrated by the accompanying drawing which, in full color, shows the upper portion of a full grown blooming plant in the upper view and a close-up view of a fully opened bloom in the lower view, the color rendition being as nearly true as can be reasonably obtained by conventional photographic procedures.

DESCRIPTION OF THE NEW PLANT

The following is a detailed description of my new variety of lily plant as observed at Arcata, Calif., with color designations according to The R.H.S. Colour Chart published by The Royal Horticultural Society of London, England, and developed with cooperation of The British Colour Council.

THE PLANT

Origin: Seedling.
Parentage:
*Seed parent.*—Enchantment.
*Pollen parent.*—Unknown.
Classification: Chalice type, Asiatic hybrid.
Form: A tall, single stem from each bulb.
Height: 1 to 3 feet, depending upon age of the bulb.
Growth: Upright and sturdy, with excellent strength.

Stem size: From about $\frac{1}{4}$ inch diameter at the base when the plant is at a height of about one foot, to about $\frac{3}{4}$ inch diameter at the base when the plant has a height of about 3 feet.
Foliage: Quantity — abundant.
*Size of leaf.*—3 to 7 inches long and about $\frac{1}{4}$ to $\frac{3}{4}$ inch wide on the stem; at the flower cluster, the leaves are 3 in number and about $1\frac{1}{2}$ to $2\frac{3}{4}$ inches long and about 1 to $1\frac{1}{4}$ inches wide.
*Shape of leaf.*—Lanceolate.
*Texture.*—Leathery.
*Aspect.*—Smooth.
Aerial bulbils produced in the leaf axils:
*Size.*—About $\frac{1}{8}$ to $\frac{1}{4}$ inch in diameter.
*Color.*—Maroon.
Stem bulblets (under ground):
*Occurrence.*—4 to 12 on each healthy, normal plant at digging time.
*Size.*—About $\frac{1}{4}$ to 1 inch in diameter.
*Color.*—White.
Bulbs:
*Size.*—About 1 to 3 inches in diameter.
*Color.*—White.

THE BUD

Form: Elongate-oblong, with an obtuse apex.
Size: About 2 to 3 inches long and about $\frac{1}{2}$ to $\frac{3}{4}$ inches in diameter.
Opening rate: Normal, tertiary and secondary buds opening successively.
Color: When sepals first divide and petals begin to unfurl — Reddish-Orange with a Golden Yellow stripe down the middle of the bud.
Pedicel: Strong and generally upright and angled about 60° from the vertical.
*Length.*—$2\frac{1}{2}$ to 4 inches.
*Number of buds.*—Usually one, occasionally two on each pedicel.

THE FLOWER

Blooming habit: Annual, blooming profusely in June.
Size of flower: Medium to large, averaging 6 to 9 inches in diameter and about $\frac{1}{2}$ inch in depth.
Shape: Generally flat with uniformly spaced petals in star arrangement.
Borne: From large bulbs, the inflorescence has a raceme arrangement for the first 2 or 3 pedicels, each of which has 1 or 2 buds, and at the top, the inflorescence breaks into an umbel cluster of 2 to 8 pedicels each with 1 bloom. Small bulbs often produce an umbel cluster only, each pedicel having a single bloom. The size of the bulb and its cultural care will determine the number of buds and blooms to be found on a particular inflorescence. From large bulbs, this plant may produce 6 to 8 open blooms at the same time and 2 to 3 open blooms in the top umbel cluster.

Petalage: Normal, 3 sepals and 3 petals.

*Form.*—Elliptical, with obtuse apex, prominent nectariferous grooves and a central longitudinal furrow bisecting each petal. The petals are about $\frac{3}{4}$ to 1 inch in width and the edges are very slightly crinkled and curled inwardly with recurved tips.

*Color.*—Upper side — the background color of the petal is Orange-Red, RHS 30A and the majority of the petals, excluding $\frac{1}{8}$ to $\frac{1}{4}$ inch of the outer edge, is streaked with Yellow-Orange, RHS 15A; with the Yellow-Orange stripes varying in width, end-to-end, from about $\frac{1}{4}$ to $\frac{1}{2}$ inch wide. Under side — the outer edge of the petal is Orange-Red, RHS 31A, and the middle of the petal is Yellow-Orange, RHS 23B. The flower color may vary, either lighter or darker, according to the soil and climate in which the plant is grown.

*Papillae.*—Present on the petals and from 4 to 8 in number.

*Texture.*—Leathery.

*Aspect.*—Velvety.

Discoloration: The flower color becomes more orangish and fades as the blossom matures.

Effect of weather: Generally the flower is not affected by wet weather, but ages as temperature rises.

Fragrance: None.

Persistence: The flowers tend to hang on and dry.

Lasting quality: 3 to 6 weeks on the plant, depending upon the size of the bulb and the temperature; 10 days to 2 weeks as a cut flower.

REPRODUCTIVE ORGANS

Stamens:

*Anthers.*—Number: six. Arrangement: orderly around the pistil. Length: about $\frac{1}{2}$ inch. Color: Gray-Orange, RHS 172A.

*Filaments.*—Length: about 2 inches.

Pistils:

*Number.*—One.

*Style.*—About 2 inches long.

*Stigma.*—Color — very pale yellow.

Ovary: Contained in a schizocarp, about $1\frac{1}{2}$ to 2 inches long and about 1 inch in diameter, dehiscing into thirds and containing 6 rows of seeds of the usual shape.

I claim:

1. A new and distinct variety of Asiatic hybrid lily plant, substantially as herein shown and described, characterized by generally yellow-orange appearing blooms of medium size having golden yellow stripes extending the length of each petal, on each side of a central furrow, over an orange-red background.

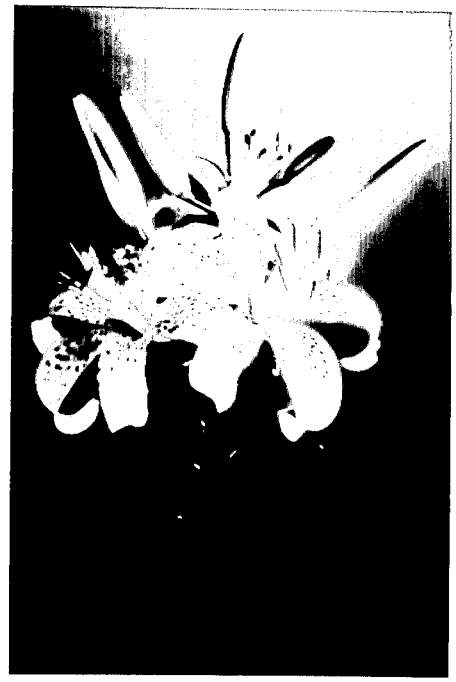
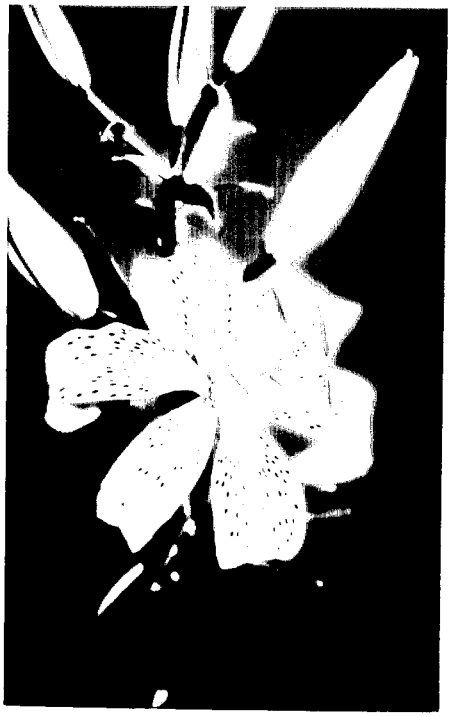

* * * * *